US007013742B2

(12) United States Patent
Beraud (10) Patent No.: US 7,013,742 B2
(45) Date of Patent: Mar. 21, 2006

(54) ACCELERATED ARTIFICIAL WEATHERING TEST SYSTEMS

(76) Inventor: Michel Pierre Paul Beraud, Station d'Essais de Vieillissement, Naturel de Bandol, 75-90 rue Cuvier, Bandol (FR) F-83150

( * ) Notice: Subject to any disclaimer, the term of this patent is extended or adjusted under 35 U.S.C. 154(b) by 31 days.

(21) Appl. No.: 10/480,571

(22) PCT Filed: Jun. 14, 2002

(86) PCT No.: PCT/FR02/02073

§ 371 (c)(1),
(2), (4) Date: Dec. 12, 2003

(87) PCT Pub. No.: WO03/016876

PCT Pub. Date: Feb. 27, 2003

(65) Prior Publication Data

US 2004/0231440 A1 Nov. 25, 2004

Related U.S. Application Data

(63) Continuation-in-part of application No. PCT/FR00/03499, filed on Dec. 13, 2000.

(30) Foreign Application Priority Data

| Jun. 14, 2001 | (FR) | ................................. 01 08234 |
| Jun. 14, 2002 | (FR) | ................................. 02 07772 |

(51) Int. Cl.
*G01N 17/00* (2006.01)
(52) U.S. Cl. .................. 73/865.6; 250/492.1; 356/244; 374/45; 374/57
(58) Field of Classification Search ............... 73/865.6; 250/492.1; 356/244; 374/45, 57
See application file for complete search history.

(56) References Cited

U.S. PATENT DOCUMENTS

| 3,886,791 A | * | 6/1975 | Grossman | .................. 73/150 R |
| 3,983,742 A | * | 10/1976 | Suga | ........................... 374/57 |
| 4,012,954 A | * | 3/1977 | Klippert | ................... 73/150 R |

(Continued)

FOREIGN PATENT DOCUMENTS

DE        32 43 722 A    5/1984

(Continued)

OTHER PUBLICATIONS

International Search Report for PCT/FR02/02073; ISA/EPO; Mailed: Dec. 23, 2002.

*Primary Examiner*—Hezron Williams
*Assistant Examiner*—David A. Rogers
(74) *Attorney, Agent, or Firm*—Harness, Dickey & Pierce, P.L.C.

(57) ABSTRACT

The invention concerns a device for exposing samples to photonic radiation for accelerated artificial weathering tests, comprising: chamber (30), a sample-holding cage (40) rotating about a horizontal axis (H—H), at least an electromagnetic radiation lamp (10) in the central part of the cage (45, 46). One improvement consists in ventilating means blowing air into the chamber (30) through the air intake orifice (50), so as to generate an air stream arriving directly on the lamp (10), then diverging about the lamp (10) to be evacuated through the fixed air outlets (31–38) at the periphery of the cage (40). Another improvement consists in the fact that the lower part of the rotary sample-holding cage is immersed in a liquid tank, such that the samples are cyclically in immersion phases into the liquid alternating with emergence phases into the air stream. The invention also concerns test devices and methods integrating said improvements.

18 Claims, 6 Drawing Sheets

U.S. PATENT DOCUMENTS

| | | | |
|---|---|---|---|
| 4,627,287 A * | 12/1986 | Suga | 73/865.6 |
| 4,704,903 A * | 11/1987 | Suga et al. | 73/159 |
| 4,760,748 A | 8/1988 | Katayanagi et al. | |
| 4,770,542 A | 9/1988 | Takagi et al. | |
| 4,843,893 A * | 7/1989 | Huber et al. | 73/865.6 |
| 4,874,952 A * | 10/1989 | Arnaud et al. | 250/455.11 |
| 5,136,886 A * | 8/1992 | Neigoff et al. | 73/865.6 |
| 5,138,892 A * | 8/1992 | Suga | 73/865.6 |
| 5,206,518 A | 4/1993 | Fedor et al. | |
| 5,476,636 A * | 12/1995 | Tomiita et al. | 422/53 |
| 5,646,358 A | 7/1997 | Tikhtman et al. | |
| 5,734,115 A * | 3/1998 | Camp et al. | 73/865.6 |
| 5,767,423 A * | 6/1998 | Camp et al. | 73/865.6 |
| 5,854,433 A * | 12/1998 | Patel et al. | 73/865.6 |
| 6,591,701 B1 * | 7/2003 | Suga | 73/865.6 |
| 6,626,052 B1 * | 9/2003 | Martin et al. | 73/865.6 |
| 6,709,631 B1 * | 3/2004 | Mori et al. | 422/53 |
| 6,863,123 B1 * | 3/2005 | Wang et al. | 165/263 |
| 2004/0123682 A1 * | 7/2004 | Grossman et al. | 73/865.6 |

FOREIGN PATENT DOCUMENTS

| | | |
|---|---|---|
| DE | 199 45 917 A | 4/2000 |
| EP | 0 289 436 A | 11/1988 |
| EP | 0 320 209 A | 6/1989 |
| EP | 0 403 281 A | 12/1990 |
| FR | 2 802 301 A | 6/2001 |
| JP | 63 222240 A | 9/1988 |

* cited by examiner

ACCELERATED ARTIFICIAL WEATHERING TEST SYSTEMS

BACKGROUND OF INVENTION

1. Technical Field

This invention relates to the field of electromagnetic radiation source devices and apparatuses for testing accelerated weathering of samples under the effect of light, and other atmospheric conditions such as temperature, humidity or water precipitation. In particular, the tests relate to the resistance of samples made of polymer materials that are essentially sensitive to ultraviolet radiation.

2. State of Prior Art

Natural weathering of materials under solar light is simulated in a known manner by exposing samples to an electromagnetic radiation source with a spectral distribution that must be carefully chosen to achieve accelerated weathering that can be correlated to weathering observed under natural conditions.

Various devices and apparatuses are known for controlling exposure to laboratory light sources. The nature of light radiation sources has an overriding influence on test conditions and fully determines operation of the devices.

Thus standard ISO 4892 that governs 'Exposure methods to laboratory light sources' for "Plastics", makes a distinction between three radiation source categories, and apart from the General Guide in Part 1 (ISO 4892-1), contains three appendices dealing with the following subjects:

Part 2: Xenon arc sources (ISO 4892-2)
Part 3: U.V. fluorescent lamps (ISO 4892-3)
Part 4: Open flame carbon arc lamps (ISO 4892-4).

In the category of carbon arc lamps, historically the oldest category, the light source is formed of several pairs of carbon electrodes, typically 2 to 4 pairs of electrodes, composed of a mix of rare earth metallic salts with surface metallisation, the opposite electrodes being arranged axially one along the prolongation of the other with a system for keeping their spacing constant as they are consumed.

The electric arc between the carbon electrodes generates radiation that contains ultraviolet rays, visible light and infrared light, while releasing a very large quantity of heat.

Consequently, the samples cannot be directly exposed to the open flame in carbon arc lamps and light must be filtered, different filters and protection elements being recommended.

ISO standard 4892-4 recommends glass filters resistant to heat, which is suitable to simulate exposure to sunlight through thick window glass, Pyrex, Corex, etc.; these glass filters must have a composition and thickness giving a specific transmission spectrum.

A series of documents related to devices for accelerated tests on stability to light and climatic agents is known in this category of devices and apparatuses equipped with carbon arc lamps, produced by the Japanese SUGA Test Instrument Co. Company.

Document U.S. Pat. No. 4,760,748 published by SUGA in 1988 and the previous documents series U.S. Pat. Nos. 4,704,903 and 3,983,742 all describe devices consisting of a large solid cylindrical frame that rotates around a light source composed of a vertical tubular funnel containing pairs of electrodes arranged longitudinally. The polymer sample test pieces are arranged in outlets formed in solid walls of this cylindrical frame.

Windows are perforated in the funnel (or stove pipe) in which the filters are located.

The funnel or the cylindrical casing that supports the glass filter elements is thus inserted between the carbon electrode arc burner and the samples that are fitted in openings in the tubular sample-holding frame to prevent the strong infrared radiation and the high release of hot air from the carbon electrodes flame from reaching the surface of the samples.

The sample-holding frame rotates around the central axis of the carbon arc burner casing, which is vertical or slightly inclined according to the recommendations in ISO 4892.4 (point 4.2). The sample-holding frame has a large overall size, about a meter and typically 96 centimeters.

Due to the large release of heat, carbon arc lamp devices have a complex double cooling system, firstly to cool the burner, and secondly to cool the samples.

Devices comprising a fixed header pipe of low-pressure arc tubes that supply ultraviolet radiation are known. This ramp of parallel tubes is arranged facing the samples to be tested.

The disadvantage of the radiation from low-pressure arc tubes is that emissivity is low and the ultraviolet spectrum is very different from the solar spectrum, which has a negative effect on the tests.

Another disadvantage is that samples cannot be exposed uniformly in these devices, such that the reproducibility of test results is not good.

Devices using Xenon arc lamps are known, which have the advantage of having a spectrum very similar to the solar spectrum when they are suitably filtered.

According to the state of recent developments in the art, it is now possible to adopt filtered medium pressure mercury vapour lamps with a spectrum very rich in ultraviolet radiation and with a good equilibrium between long U.V.A. type ultraviolets and short U.V.B. type ultraviolets, in an equivalent manner, to achieve good reproduction of weathering due to sunlight.

Weathering test apparatuses are known in which samples are mounted on a vertical cylindrical sample holder rotating around tubular Xenon arc lamps arranged vertically.

Rotation of samples around Xenon lamps provides a means of achieving uniform exposure to radiation.

However, these lamps release a great deal of heat and open circuit or closed circuit air circulation is necessary to keep the samples at a controlled temperature.

These apparatuses have the disadvantage that they expose the samples to variable temperatures.

The ventilation circuit comprises an air intake zone above the cylindrical sample-holder that creates a vertical air stream like in a funnel. The air stream warms up at it moves vertically along the lamps and the samples, so that the samples at the top of the sample holder are necessarily warmer than the samples at the bottom. Therefore, identical samples at different heights are subjected to different temperatures, and this also affects the reproducibility of the tests. In practice, some users are obliged to interrupt the tests to invert the samples being tested, and swapping the positions of the samples between the top and bottom of the sample holder.

Devices are also known comprising a parallelepiped shaped test chamber with mercury lamps arranged vertically in the four corners of the chamber around a small rotating sample-holding cylinder arranged in the centre of the chamber. The lamps and the outer face of the samples are cooled by air circulation ventilated with air inlets open in the sidewalls of the chamber and an air opening covering the entire sample-holding cylinder at the top of the chamber.

One disadvantage of this device is that it is excessively large compared with the small area of the samples being tested.

This device also has the disadvantage that it has large light energy losses, since more than 75% of the light does not travel directly towards the sample holder.

Consequently, the efficiency of this device per unit area of samples being tested is low, when the depreciation of the equipment plus energy expenses are included, making the tests expensive.

There are also apparatuses comprising a rectangular test chamber in which a cylindrical sample-holding cage is mounted, free to rotate about a solid drive shaft. A laminar air stream travelling vertically between openings formed along the axis of the generating lines of the cylinder at the floor and at the top of the chamber passes along the samples, in order to isolate the samples from the hot air stream from the lamp and to homogenize the test temperatures.

However despite the laminar air stream, this instrument still has the disadvantage that it exposes the samples to different temperatures, the laminar air stream becoming warmed further as it comes into contact with samples exposed to bright light radiation. In practice, samples arranged at the top of the cage are thus exposed to a temperature several degrees higher than the samples at the bottom of the cage.

Patent EP-0 320 209 thus describes an atmospheric test cabinet comprising a sample-holding rack or basket rotating around a vertically arranged xenon light tube. The samples are cooled by a laminar air stream that passes vertically along the internal walls of the samples arranged along the straight edges of the rack. The air stream has a limited flow rate for reasons of economy.

This vertical low flow rate laminar air stream test cabinet has the disadvantage that it does not provide efficient cooling of the samples and it induces temperature differences between samples at the bottom and samples at the top of the rack.

Patent U.S. Pat. No. 4,760,748 describes another accelerated weathering test device also comprising a cylindrical sample-holding frame free to rotate about a vertical axis and light tubes, with an ascending laminar air stream cooling the inner face of the samples. The cylindrical frame comprises solid walls through which two rows of openings are perforated, firstly to place the samples and secondly to form intake orifices for a secondary air stream.

The device is cooled by providing it with a double flow air circulation system, with an ascending main air column rising in the sample-holding cylinder, passing along the inner face of the samples and a peripheral secondary air stream that strikes the outer face of the samples. The makeup secondary air stream originates from a cooled air source. The secondary air stream is created by a suction effect provoked at the orifices of the cylinder by ascension of the main air column. The size of the orifices can be varied to modulate the peripheral secondary air stream as a function of the ascending main air stream.

The disadvantage of this device is the complexity and the particularly large size of its double flow air circulation system.

Another disadvantage with this device is that its testing space and the number of samples that it can hold are very limited, considering the large size of the cabinet including its equipment for evacuation of air near the top, the blower and the rotation drive near the bottom, and the peripheral air circulation system and the lateral cooling air source.

This double air stream cooling system has another disadvantage, which is that it induces significant temperature differences between the irradiated inner face and the cooled outer face of the samples.

German document DE-A-32 43 722 describes a very different device for tests on resistance to light and the weather, including a large ventilated chamber in which a horizontal assembly is arranged comprising a ring of light tubes inserted between two concentric horizontal air ducts and a sample-holding drum mounted free to rotate about the horizontal ducts. The two ducts are connected to a fan and communicate with each other and with the outside of the chamber, such that external air is blown into the first duct and is then returned and enters the space between the first and the second duct to pass along the light tubes, cooling them on its way back towards the outside.

The samples arranged on the outer drum are cooled separately by another vertical air stream that circulates in a circuit provided with another fan and a cooling exchanger, and possibly heating means.

Therefore, this device comprises two cooling air circulation systems, one cooling the samples and the other cooling the light tubes.

In this device, the light tubes and a sprinkler system are arranged in the ducts that separate them from the samples, but this has the disadvantage that it hinders light exposure of the samples and reduces the efficiency of the system.

Another disadvantage of this device is that the vertical air stream that passes through the sample-holding drum does not cool the samples efficiently.

The purpose of this invention is to make a device for exposure to radiation to test weathering of samples to submit the samples to a uniform temperature and irradiation, without the above mentioned disadvantages.

In particular, the purpose of the invention is to enable efficient ventilation of the samples during tests carried out with the device.

Another purpose of the invention is to obtain a device with a small number of lamps and a compact size.

Another parallel purpose of the invention is to obtain a device with a simple design and a high light efficiency as a function of the surface area of exposed samples so as to reduce the cost of the tests.

Finally, another purpose of the invention is to facilitate manipulation of samples prior to the weathering tests.

BRIEF DESCRIPTION OF THE INVENTION

Briefly, according to the invention, these objectives are achieved by making a device with a rotating sample-holding cage with an axis of rotation that is preferably horizontal such that the samples are cyclically in the upper part and then in the lower part of the chamber, so that this eliminates inherent temperature differences, and more essentially by an arrangement in which the device is subjected to an air stream arriving directly on the lamp, blown through an axial orifice, and then diverging around the lamp and passing outwards through the radial prolongation of the sample-holding cage, through air passage openings (also called air openings or openings or air evacuation openings) located around the periphery of the cage, such that the temperature of the air stream increases as it comes into contact with the lamp before going around the samples, thus increasing their temperature and then keeping the temperature uniform. Preferably, the air circulation system forms a turbulent air stream around the centreline of the cage.

The air stream enters the device at the centre of the cage parallel to its axis, and according to the invention essentially having an axial component in the central part of the cage, and then exits from the cage at its periphery by arriving transverse to the axis and essentially having tangential and/or radial components at the periphery of the cage, to create a symmetric and uniform air stream.

The invention is made with a device for exposure to photonic radiation for accelerated artificial weathering tests of samples, comprising:

a chamber, a sample-holding cage rotating around an axis that will be approximately horizontal in operation, means of fixing the position of at least one low power arc lamp with a power of the order of a few tens to about a thousand watts, and particularly comprising a mercury vapour lamp or a mercury compound vapour lamp near the centre of the cage, and of supplying it with electricity, and an air circulation system comprising an air passage arranged along the axial prolongation of the central part of the cage and several fixed air passage openings arranged in the radial prolongation of the periphery of the cage, the air circulation being designed to keep samples in the chamber at a uniform temperature of a few tens of degrees Celsius, the improvement being that the ventilation means blow air into the chamber through the orifice that forms an air intake orifice arranged approximately parallel to the horizontal axis, the lamp being placed along the immediate axial prolongation of the air intake orifice, so as to generate an air stream arriving directly on the lamp and approximately parallel to the axis along the central part of the cage, the air stream diverging around the lamp and being evacuated approximately perpendicular to the axis through fixed openings that form air openings around the periphery of the cage, such that the temperature of the air stream increases as it comes into contact with the lamp, before going around the samples, thus increasing their temperature and then keeping the temperature uniform.

According to another essential improvement, the device comprises a tank arranged in the lower part of the chamber to surround the lower part of the rotating sample-holding cage.

Advantageously, this arrangement means that the samples may alternately be immersed in the liquid and then exposed to the air stream and to U.V. radiation of the lamp.

Advantageously, with this improvement a series of test protocols can be performed with different natures of liquid corresponding to degradation factors and multiple variants to the alternating immersion/emersion, and light/darkness phases.

According to this improvement, the best embodiment of the invention is then obtained with exposure to photonic radiation and climatic agents to perform accelerated artificial weathering tests on samples comprising:

a chamber, a sample-holding cage rotating about an axis (that will be arranged approximately horizontally in operation), means of fixing the position and for providing an electrical power supply to at least one electromagnetic radiation lamp in the central part of the cage, along the horizontal axis, means of generating a simple direct air stream in the chamber, the air stream being propagated directly and freely from the internal central part to the external peripheral part of the cage, and a tank arranged in the lower part of the device intended to contain a liquid volume so that the lower part of the rotating sample-holding cage can be immersed, such that the samples cyclically alternate between immersion phases in the liquid and emersion phases in the air stream, so that the resistance of samples to weathering under the action of immersion and photonic radiation can be tested (the resistance to climatic agents and stability to photonic radiation of the samples).

Preferably, the tank is formed of a crescent-shaped basin fixed in the lower part of the plate of the device.

Liquid supply means are provided to keep the liquid level in the tank approximately constant.

Thus advantageously, rotation of the sample-holding cage makes it possible to alternate phases in which samples are exposed to immersion in water with phases in which they are exposed to the air stream, under continuous exposure to photonic radiation from the lamp.

Preferably, the photonic radiation source is a low power mercury arc lamp with power of the order of several tens of watts to about a thousand watts.

Advantageously, the air stream diverging around the lamp comprises essentially a component approximately parallel to the axis, in the central part of the cage close to the lamp, while the said air stream comprises essentially components approximately perpendicular to the axis, at the periphery of the cage near the samples.

Advantageously, the air stream enters the centre of the cage parallel to the axis, having essentially an axial component in the central part of the cage, and is then evacuated at the periphery of the cage arriving transverse to the axis and essentially having tangential and/or radial components at the periphery of the cage, to create a symmetric and uniform air stream.

Advantageously, all positioning and power supply means of the lamp, ventilation and air circulation means and cage rotation drive means are all arranged in the same axial part of the device.

Advantageously, all positioning and power supply means of the lamp, ventilation and air circulation and cage rotation drive means are all arranged in line along the horizontal axis of the device.

Preferably, the cage is installed free to rotate on a hub hollowed out along the axial direction, the air stream being blown through the axial hole through the hub.

Preferably, the air circulation system comprises ventilation means arranged in the hollowed out hole in the hub, so as to blow air towards the chamber.

Preferably, the air circulation system is in open circuit, which means that fresh air in the laboratory can advantageously be drawn in.

Alternatively, the air circulation system can operate in a closed circuit.

Preferably, the air circulation system comprises a series of several fixed air openings arranged regularly around the periphery of the cage with a symmetry of revolution about the axis, each fixed air opening being oriented in a direction between the radial direction and the tangential direction around the periphery of the cage. An air outlet duct is arranged in the axial prolongation of the central part of the cage, the duct being arranged in a direction parallel to the axis.

According to the preferred embodiment of the invention, the cylindrical chamber comprises air openings arranged approximately at the periphery of the cage, each air outlet opening being oriented in a non-radial direction. The depth, aperture and angle of inclination relative to the radial direction, of each air outlet opening will be such that the radiation from each lamp positioned in the central part of the cage does not pass through the opening and does not escape directly outside the chamber.

According to the preferred embodiment of the invention, the cage comprises central elements and peripheral elements extending in the radial direction and connected by radial elements, the central and peripheral elements extending into a single half-space delimited by the radial elements.

According to the preferred embodiment, the cage comprises circular elements with different diameters so that the samples can be arranged at different angles of exposure.

According to one advantageous alternative, the central elements of the cage are developed in spirals around the axis.

According to the preferred embodiment of the invention, the cage is connected to the hub through a declutchable drive mechanism allowing free rotation of the cage.

Advantageously, the mechanism comprises rotation declutching means under the effect of a limited axial torque between the cage and the hub.

Advantageously, the mechanism comprises means of declutching or desolidarisation in translation, under the effect of a limited axial force between the cage and the hub.

According to one alternative embodiment, the device comprises a water tank arranged so that part of the cage is immersed.

Preferably, a temperature sensor is arranged fixed to the inside of the chamber at a location close to the periphery of the rotating sample-holding cage.

A slaving circuit is provided to control the temperature as a function of a measurement and a temperature set value, acting on the electrical power supply to the lamp and/or switching the ventilation means on or off. The electrical power supply circuit includes a ballast to regulate the power supply current to a medium pressure mercury vapour lamp.

According to one variant, the air circulation system comprises means of heating the air stream.

According to another variant, the air circulation system includes means of cooling the air stream.

The invention also applies to a method of carrying out sample weathering tests with the special feature that it implements such a radiation exposure device.

And particularly, and more precisely, the improvement to the best embodiment of the invention makes it possible to adopt a method for carrying out accelerated artificial weathering tests on samples in which the samples are exposed to photonic radiation and climatic agents, characterized in that it includes steps consisting of:
  arranging the samples on a sample-holding cage rotating about an approximately horizontal axis,
  positioning at least one photonic radiation lamp in a fixed position in the central part of the cage along the horizontal rotation axis, and supplying electrical power to it,
  generating a simple direct air stream propagating directly and freely from the central inner part of the cage towards the outer peripheral part of the cage, and,
  immersing a lower portion of the rotating sample-holding cage in a liquid bath, so as to cyclically alternate phases in which the samples are immersed in the liquid, with phases in which the samples are exposed to the air stream.

Thus, the lower part of the cage is immersed in a tank that can contain a liquid volume.

The liquid level in the lower part of the cage is kept approximately constant.

Advantageously, rotation of the sample-holding cage enables an alternation of phases in which the samples are immersed in the liquid and phases in which the samples are exposed to the air stream, at the same time as the rotating samples are exposed to photonic radiation from the lamp.

According to one test protocol, it is intended that air stream temperature measurements should be carried out at one or more locations close to the periphery of the rotating sample-holding cage.

Subsequently, it is possible to regulate the temperature of the air stream by slaving the lamp electrical power supply and/or the air stream generation means to the temperature.

More precisely, a set test temperature of the order of 35° C. to 100° C. can be maintained.

According to another test protocol, the temperature can be varied between extreme climatic values.

Alternately, according to another test protocol, the temperature can be allowed to vary without control.

Preferably, according to the test protocol, the duration of the immersion phase represents a proportion of the order of a few hundredths (or less) to half the duration of the rotation cycle of the sample-holding cage.

According to the preferred protocol, the duration of the immersion phase represents a proportion of the order of one tenth (or a few hundredths) to a third of the duration of the rotation cycle of the sample-holding cage.

Furthermore depending on the test protocol, the rotation speed of the sample-holding cage is less than one revolution per minute.

According to the preferred protocol, the rotation speed of the sample-holding cage is of the order of one tenth of a revolution to ten revolutions per hour.

Furthermore, more fundamentally and advantageously, according to the preferred test protocol, phases of exposure to photonic radiation from the lamp may be alternated with darkness phases.

Advantageously, the duration of the darkness phase represents a proportion of the order of between one tenth and one half of the duration of the cycle of alternating exposure to radiation and darkness phases.

According to one test protocol, the darkness phase coincides at least partially with the immersion phase.

The improvement to the test method includes several test protocols with immersion phases into:
  pure water with a hydrogen potential equal to seven (pH=7.0),
  water containing dissolved oxygen,
  possibly liquid containing oxygenated water,
  acidulated water with a hydrogen potential of less than seven (pH<7),
  water containing suspended solids, and
  water containing one or more pollutants.

The nature of the pollutant(s) is chosen from among the group of pollutants comprising:
  ozone,
  carbon dioxide,
  nitrogen oxides,
  sulphur trioxide and sulphur dioxide,
  chlorides,
  fluorine compounds,
  phosphorus compounds,
  insecticides,
  pesticides and,
  aerosols.

BRIEF DESCRIPTION OF THE FIGURES

Other objectives, characteristics and advantages of the invention will become clear after reading the following description of an embodiment, given solely as a non-limitative example, that is given with reference to the attached drawings in which.

DETAILED DESCRIPTION OF PREFERRED EMBODIMENTS

FIGS. 1 to 5 clearly show that the device according to the invention is preferably globally circular and symmetric in revolution around an axis H—H that will advantageously be in the horizontal direction.

In the following description of the embodiment and operation, to simplify matters it will be assumed that the device is symmetric in revolution about the H—H axis, but more complex geometries could be envisaged by those skilled in the art without going outside the scope of this invention.

Figure 1A:
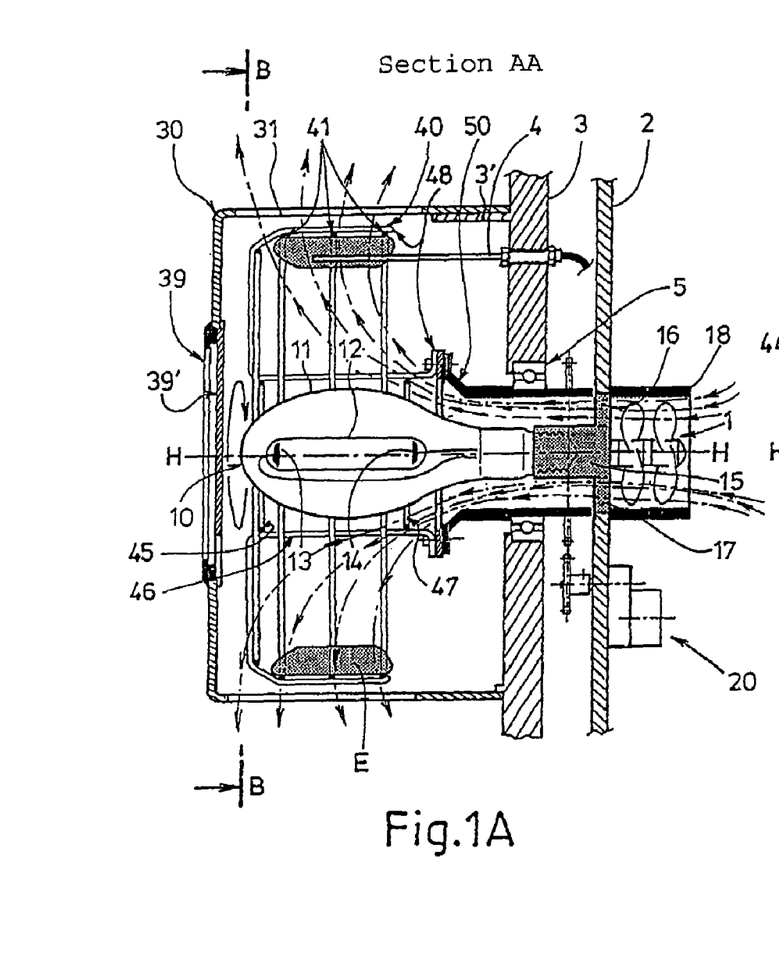
FIG. 1A diagrammatically shows an axial sectional view through the radiation exposure device according to the invention, FIG. 1B diagrammatically shows a cross-sectional front view of the device according to the invention.

FIG. 1A thus shows that the device according to the invention comprises a cylindrical and circular chamber 30. Alternately, the device may comprise a cylindrical chamber with a square, rectangular or other section. The chamber comprises a removable cover, preferably in the form of a tank, that is hermetically fixed onto a fixed ring plate 3. The chamber 30 contains a circular-shaped sample-holding cage 40 that can be made according to the example shown in FIGS. 1A, 2A and 4, from a framework of metallic rods 41 to 48 bent in the form of circular elements 41, 43, 45, 47 and 49, and curved elements 48 arranged in quarters and fixed to each other.

The cage 40 is fixed to a hub 50 through a circular drive part 49 and a declutchable mechanism.

The hub 50 is mounted free in rotation, possibly on a ball or roller bearing 5, on the plate or plates 2—3 that provide a fixed support.

The hub 50 is driven in rotation by a drive system comprising an offset motor 20 connected through a gear or chain transmission 21, 22.

According to one preferred embodiment of the invention, the hub 50 is fully hollowed out in the axial direction, the hole forming an inlet duct for the air stream incoming into the chamber.

Furthermore, according to the preferred embodiment, the central part of the sample-holding cage 40 is empty, there is no rod forming part of the frame passing through the central part of the cage that is in line with the hollowed out part of the hub 50.

According to the invention, one or several electromagnetic radiation lamps 10 can be fixed in the central part of the rotating cage 40.

The lamp(s) 10 is or are connected, in other words fixed and electrically powered, directly through an axial part 15 with radial arms 16, 17 in daisy formation connected to the fixed support plate 2, or indirectly through the body 18 of the fan 1.

If a single ultraviolet lamp 10 is fitted on the device according to the invention, it is preferable that the lamp 10, generally tubular or symmetric in revolution, should be placed in the central part of the cage, the axis of the lamp being arranged along the axis H—H of the cage 40.

If one or several lamps are used on the device according to the invention, it is preferable that the lamps should be arranged symmetrically around the centreline of the cage and parallel to the said axis H—H.

In one particularly advantageous embodiment, the arrangement of the lamp(s) 10 in the central part of the sample-holding cage 40 on or around the axis of rotation H—H, is such that the rotating samples can be exposed to a perfectly homogenous light flux (provided that the samples are arranged parallel to the axis and at the same radial distance from it).

According to the invention, it is also required that the device should include air blowing means 1 aligned with the hole formed in the hub 50.

A fan could be mounted behind the hollowed out part of the hub 50 and aligned with it, to draw in air from the outside and to blow the air stream back into the chamber 30 through the air duct hollowed out in the hub 50.

The fan can be fixed to the fixed back plate 2.

Figures 2A, 2B:
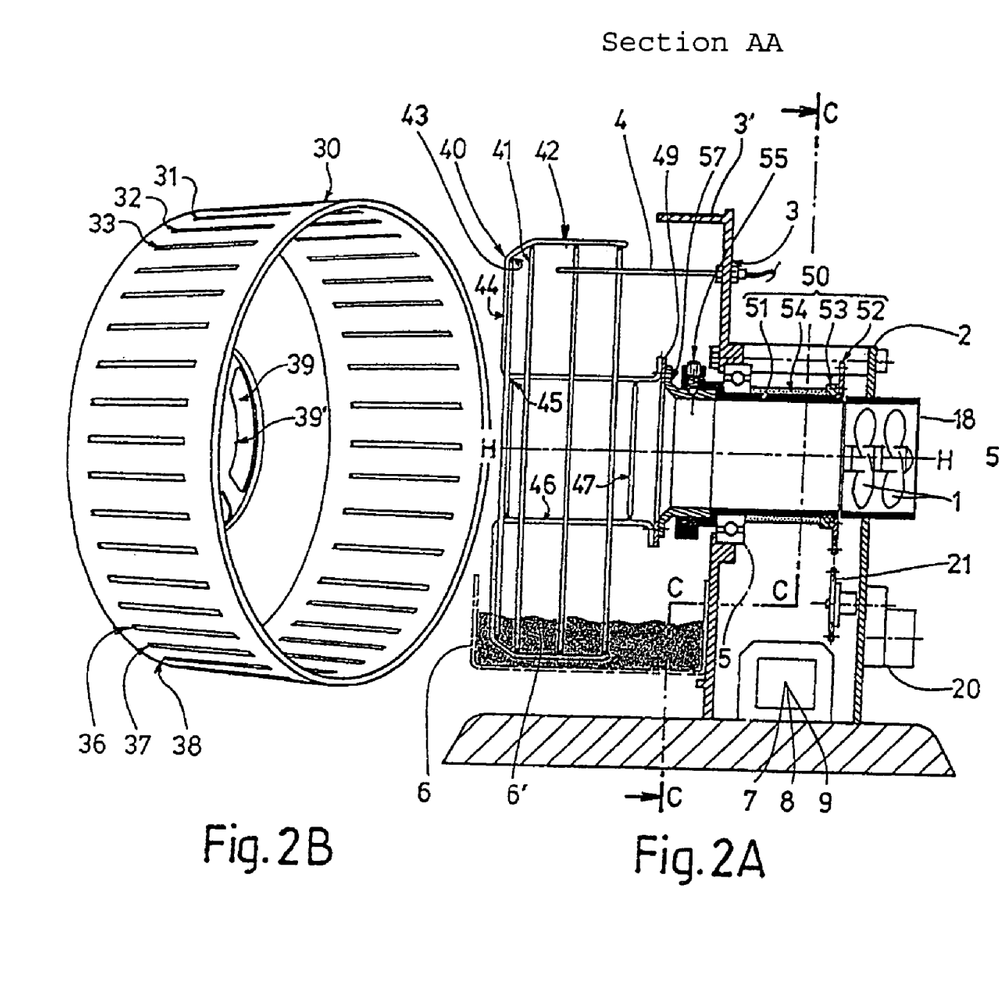
FIGS. 2B, 2A and 2C show views of an embodiment of the device according to the invention with the cover retracted, FIG. 2A showing an axial section of the device without the cover and without the lamp holder, FIG. 2B showing a three-quarter view looking inwards with the cover retracted, FIG. 2C showing a cross-sectional view of the drive system of the device, looking backwards along line C—C in FIG. 2A, FIGS. 3A and 3B show a lateral and cross-sectional view of details of an advantageous embodiment of the cover for a device according to the invention.

According to the example embodiment in FIGS. 1A and 2A, two fans can be mounted in series behind the hollowed out part of the hub 50. The second fan advantageously forms a makeup or standby fan.

The advantage of this arrangement is to increase the power on several levels and to increase the reliability in the case of a fan failure.

This arrangement means that an air filter (not shown) can be inserted in order to retain particles entrained by the air stream before arriving in the chamber 30.

Advantageously, the central parts of the cage 40 and the hub 50, and their prolongations, are completely empty except for the lamp holder, to allow the air stream to pass freely.

Thus, according to the invention, the air stream arrives at the centre of the cage 40 along the axial direction H—H, the device advantageously comprising a cage 40 and a hub 50 for which the central part is completely hollowed out.

Furthermore, the invention requires that air evacuation openings 31, 32, 33, 36, 37, 38 should be arranged around the periphery of the cage 40.

According to the preferred embodiment of the invention, the cylindrical chamber 30 also comprises openings 31, 32, 33, 36, 37, 38, in other words air outlet openings drilled around the cylindrical or quasi-cylindrical (slightly conical) periphery of the cover or more generally the chamber 30.

During the tests, the samples E will be arranged around the periphery of the cage, fixing them to circular elements 41 of the cage frame, particularly using clamps.

Figure 1B:
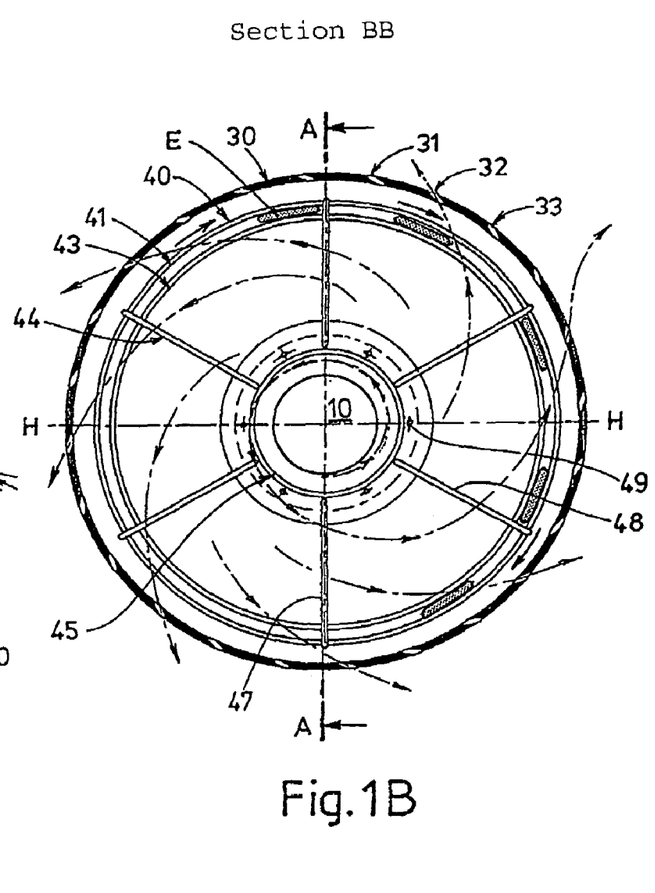

It is generally considered that the samples are cut into plates or cards, generally plane in shape, such that the samples occupy secant or tangential positions around the periphery of the circular cage 40 as illustrated in FIG. 1B.

Therefore during operation, the samples E are in a tangential or secant position around the periphery of the cage 40, the cage is rotated and the air blower means 1 start air intake flow around the H—H axis of the cage 40, the lamp 10 and the hub 50.

Therefore according to the improvement to the invention, air arrives directly on the lamp along an axial direction, and therefore approximately horizontally, before reaching the central part of the cage.

The air stream then advantageously cools the arc lamp that is typically at a temperature up to the order of one to several hundreds of degrees Celsius.

Advantageously, medium pressure mercury vapour lamps or H.M.I. (Hydragyrum Medium arc-length Iodide—metal halide) lamps can be used, in other words arc lamps in which the vapour is formed from an alloy or a metal halide compound, particularly iodide and mercury.

These lamps have the important advantage that they operate at a lower power than arc or xenon lamps. mercury vapour or mercury compound vapour lamp bulbs are smaller and are available with bases that fit E40 sockets, according to the very widespread European standard in which sodium lamps and conventional incandescent lamps can also be fitted.

The essential advantages of light sources consisting of Mercury arc lamps and metal halide lamps are that they have a very high efficiency, a well distributed spectrum with an equilibrium between U.V.A and U.V.B., very little infrared emission and consequently very low heat release.

These particularly interesting properties make these lamps ideal for equipment used for accelerated weathering tests. One essential advantage is that their low heat release means that they can be used exposed, unlike sources according to prior art.

The air stream entering the chamber then increases in temperature on contact with the lamp 10 by absorbing the released heat power, so that it can easily reach average temperatures of the order of several tens to one or two hundred degrees Celsius.

Typically, under ambient laboratory conditions at 28° C., the external air stream entering the chamber can thus be heated on contact with the lamp, to reach a temperature of the order of several tens of degrees to about a hundred degrees Celsius.

This result is a major advantage of the invention, since photo-weathering test standards recommend that polymer tests should be carried out at temperatures of about 63° C. or 83° C. or between 80° C. and 100° C., so that conditions are similar to the conditions in a passenger compartment of a car exposed to the sun.

The main advantage of the invention is thus to provide a simple air circulation system that combines evacuation of heat released by the lamp with regulation of the sample temperature by increasing their temperature to an optimum temperature to accelerate tests of polymer samples, and then maintaining this temperature within close limits once operating conditions have been set up.

Note that the device uses several low power lamps with powers of the order of several tens to several hundreds of watts, typically 250 W or 400 W, such that the quantity of heat energy to be dissipated is relatively low and the temperature remains stable.

Devices according to the state of the art using Xenon arc lamps or Carbon arc torches have a low efficiency, which requires a high electrical power and large capacity cooling equipment that invariably causes instability and large variations in the temperature of the samples during the test.

The adoption of low power arc lamps such as medium pressure mercury lamps advantageously means that the lamp can be air cooled, and this heated air stream can be used directly to bring the samples up to the test temperature and hold them at this temperature.

Thus, the invention requires that the air stream should diverge around the lamp in a direction perpendicular to the H—H axis to join the samples directly and to moderate their temperature.

The air stream is evacuated through air outlets around the periphery of the chamber 30. As the air stream escapes, it comes into contact with the samples E orthogonally or at an angle of incidence relative to their plane as illustrated in FIG. 1B.

Advantageously, the incidence of the air stream on the samples E improves heat exchanges.

Therefore, unlike devices according to the state of the art, the samples E are not affected by a laminar air stream, but are submitted to an incident and turbulent air stream.

For some embodiments, the air outlet flow can be strictly radial at the samples E arranged around the periphery of the cage 40.

This case arises in particular when each air opening 31, 32, 33, 36–38 is formed radially in the cylindrical part of the chamber 30, provided that the rotation speed of the cage 40 does not modify the air circulation.

For other embodiments, the air inlet flow at the periphery of the sample-holding cage 40 comprises a radial component and also a tangential component, such that the samples are subjected to an air stream at a specific angle of incidence.

In the preferred embodiment, it is thus planned that air passage openings 31, 32, 33, 36, 37, 38 should be non-radial and provided around the periphery of the cylindrical chamber 30.

Figure 3A:
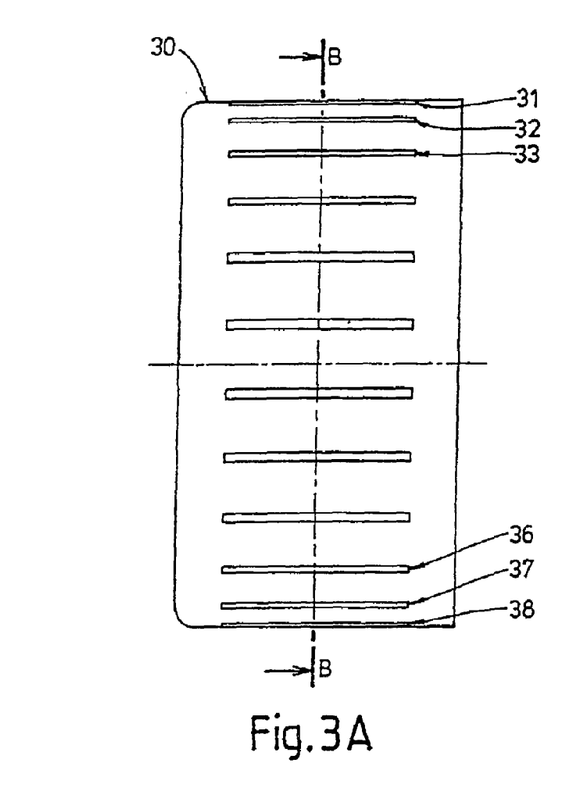
Figure 3B:
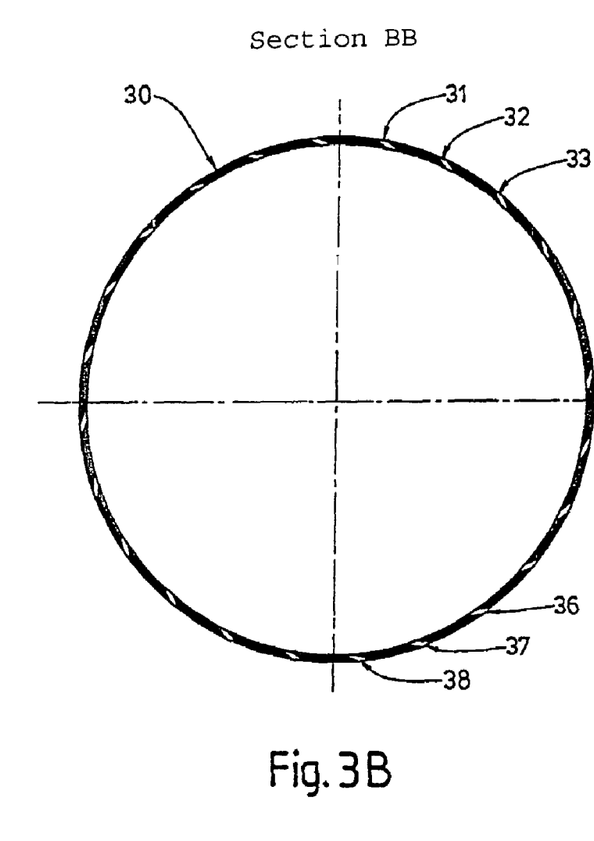

FIGS. 3A and 3B thus show that the quasi-cylindrical periphery of the cover of the chamber 30 is interrupted by narrow air passage openings 31, 32, 33, 36, 37, 38 forming openings along the axial direction, these openings having the special feature that they do not penetrate along a radial plane, but along a direction oblique to the radial direction; under limiting conditions, the openings 31, 32, 33, 36, 37, 38 could be almost tangential to the circular part of the cover.

Advantageously, the air passage openings 31, 32, 33, 36, 37, 38 which are oblique enable the air inlet flow to have tangential and radial components at the position of the samples E arranged around the periphery of the cage 40.

Air circulation is thus advantageously like an anticyclone movement around the axis of the cage, which optimises heat exchanges at the samples.

Another essential advantage of the oblique arrangement of the air passage openings 31, 32, 33, 36, 37, 38 at the periphery of the cylindrical chamber 30 is that it prevents the possibility of radiation from the lamp 10 escaping directly, while allowing air to pass, in the same way as the strips in a Venetian blind or the slats in a shutter.

In the preferred embodiment of the invention, each air passage opening 31 has a small aperture but is at a large angle of inclination from the radial direction and has a large depth, such that direct radiation from each lamp 10 positioned in the central part of the cage cannot pass through the opening 31 and cannot escape from the chamber.

Furthermore, as illustrated on FIG. 2A, the cover optionally includes a central window 39 made of anti-U.V. glass.

Advantageously this window 39 made of glass that stops the passage of ultraviolet radiation, can be used to observe the samples being tested while being protected from harmful radiation from the lamp.

Advantageously, the central part of the window 39 may be masked by a central part 39' fixed to the cover by radial arms in daisy formation as shown in FIG. 2B.

The cover is preferably made by stamping steel plate, which results in a slightly conical-shaped, quasi-cylindrical cover.

This lightweight fabrication method has the advantage of limiting the price of the equipment and investments in weathering tests.

Figure 4A:
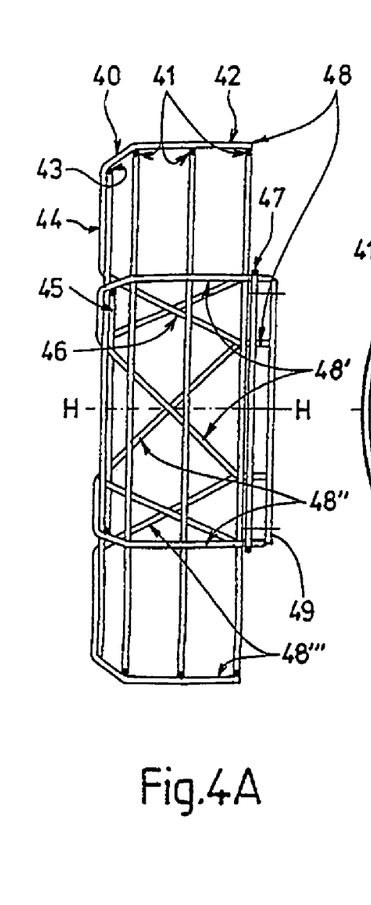
FIGS. 4A, 4B and 4C show a side view, a front view and an isometric view respectively of an advantageous embodiment of the sample-holding cage for the device according to the invention.
Figures 4B, 4C:
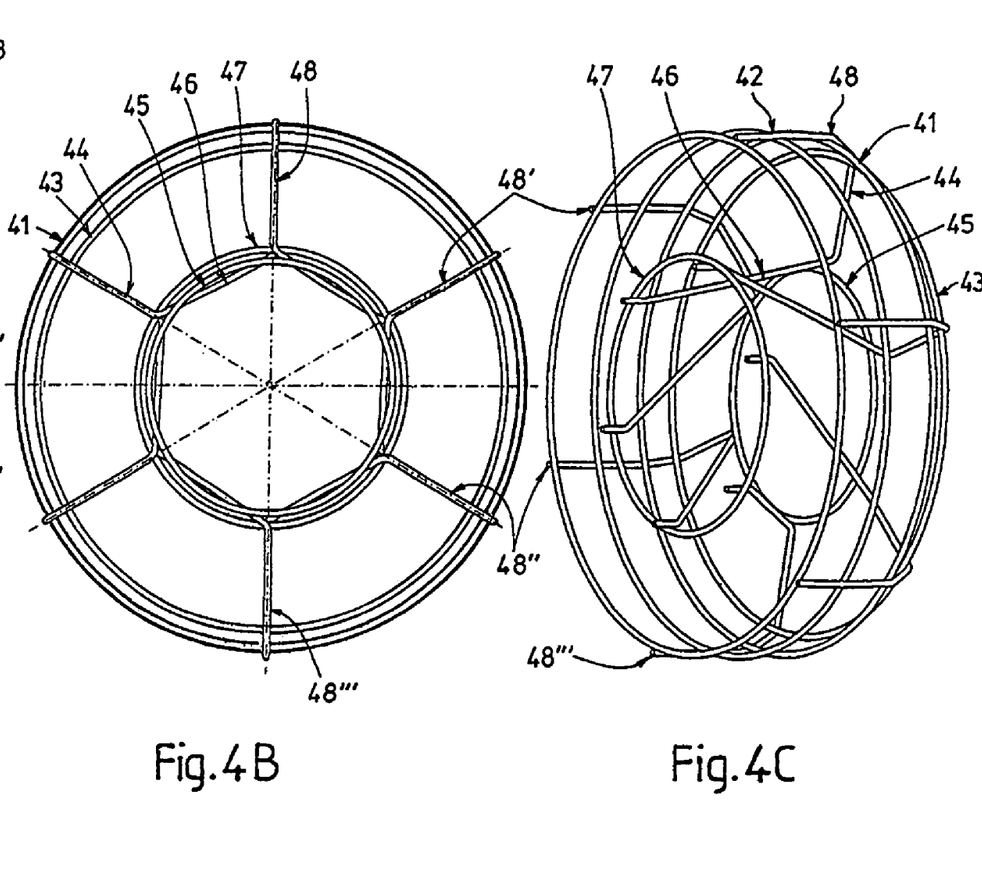

FIGS. 4A and 4B show that the cage 40 of the device is preferably made from semi-rigid metallic wires or rods 41 to 48.

The main advantage of this embodiment is that it limits the weight of the cage 40 and therefore the size of the drive motor 20.

This type of embodiment also facilitates air circulation and handling of samples.

This lightweight fabrication method also has the advantage that it limits the cost of the equipment.

In the first embodiment illustrated in FIGS. 1A, 1B and 2A, the cage 40 has a special umbrella-shaped framework.

The framework comprises the metallic rods 48 which are curved (called below curved rods) and which are arranged in quarters along radial planes so as to radiate around the hollowed out central part of the cage 40.

As shown in FIG. 4A, each curved rod 48 comprises a central strand 46 extending parallel to the H—H axis to the limit of the hollowed out central part of the cage 40. The central strand 46 is prolonged by a radial strand 44 extending in the radial direction on the opposite side of the centre. The radial strand 44 is itself connected to or prolonged by a peripheral strand 42 parallel to the axis, that delimits the periphery of the cage 40.

The special feature of the framework of the cage 40 in FIGS. 1A to 2A is that the central strand 46 and the peripheral strand 42 of each curved rod 48 are located in the same half-space delimited by the plane defined by the radial strands 44. Therefore, each curved rod 48 is in the shape of a hook.

Subsequently, the circular rods or elements 41 and 43 are fixed particularly by welding, to the peripheral strands 42 of the curved rods or elements 48 to form the framework of the circular cage 40. Similarly, the small diameter circular rods 45 and 47 may be fixed with the central strands 46 of the curved rods 48 to complete formation of the framework and advantageously to increase the stiffness of the cage 40.

Preferably, depending on the embodiment illustrated in FIGS. 1A and 2A, the cage comprises circular elements 41 and 43 with different diameters to form a multi-position framework for the samples. Thus, plane samples can be positioned perfectly parallel to the H—H axis by fixing them to elements 41 with the same diameter or in an oblique position from the axis by fixing them firstly to a large diameter element 41 and secondly to a small diameter element 43.

Advantageously, this multi-position framework means that samples with different lengths can be arranged at different angles of incidence of radiation and at different distances from the light source, so that samples with different lengths can be exposed to the same light power per unit area.

Finally, the central strands 46 of the cage framework are fixed by gluing or welding, or are fastened by any other means, onto a part in the shape of a washer that will be fixed to the hub 50.

This type of umbrella-shaped cage framework can advantageously be used to arrange instruments 4 fixed to the rotating cage.

The sensor or actuator type instruments are fixed to the fixed support ring plate 3 of the device and project from the plate (parallel to or oblique to the H—H axis) to engage inside the rotating cage 40 without affecting the rotation.

Thus, advantageously, a temperature probe 4 can be fixed onto the ring shaped plate 3 (called below ring plate 3) above the axial lamp 10, the active end of the probe projecting forwards between the lamp 10 and the samples E without preventing rotation of the umbrella-shaped cage.

Another example (not illustrated) includes a water sprinkling ramp below and parallel to the lamp 10, by fixing it to the ring plate 3 to connect it to a water inlet.

Advantageously, the ramp is thus fixed within the rotating cage parallel to the plane of the samples E, that are then regularly sprayed over their entire surface during each rotation cycle.

Furthermore, according to one improved embodiment illustrated in FIGS. 4A, 4B and 4C, the central strands 46 of the curved rods 48 are not arranged parallel to the H—H axis, but are arranged in spirals around the H—H axis of the cage 40.

The advantage of this type of improvement is that it avoids part of a sample from being placed in the shade due to the central strand 46 of a curved rod 48. The electromagnetic radiation from the central lamp thus reaches each sample uniformly, regardless of its position around the periphery of the cage.

Figure 2C:
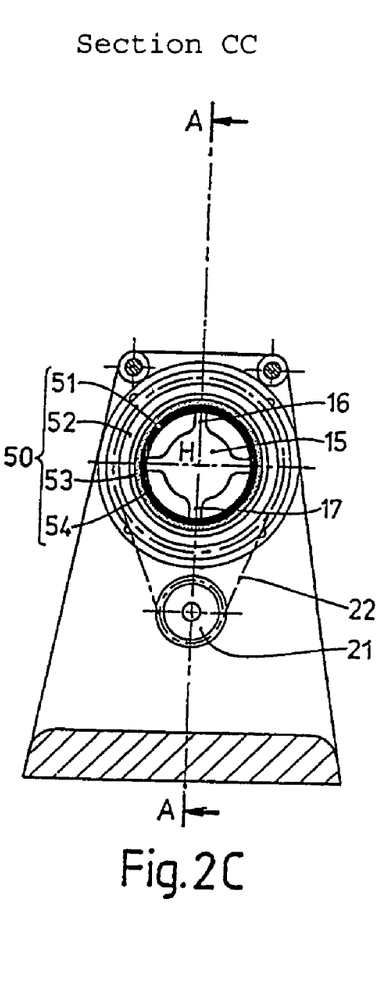

The cage 40 is mechanically rotated by a drive chain that comprises special arrangements as illustrated in FIGS. 2A and 2C.

Advantageously, the drive motor 20 is offset instead of being located along the H—H axis of the cage 40.

This means that the hollowed out central portion of the device and its prolongation can be completely free, to avoid hindering air circulation.

The motor 20 is fixed to a fixed support ring plate 2. The motor output gear drives a crown wheel or a toothed drive plate 52 fixed to the hub 50.

Transmission may be made either directly by gearwheels, with the gearwheel and the toothed drive plate 52 being in contact with each other, or indirectly through a chain, or a tensioned belt between a gearwheel and a grooved crown wheel as illustrated in FIG. 2C, or by any other transmission means.

Figure 5A:
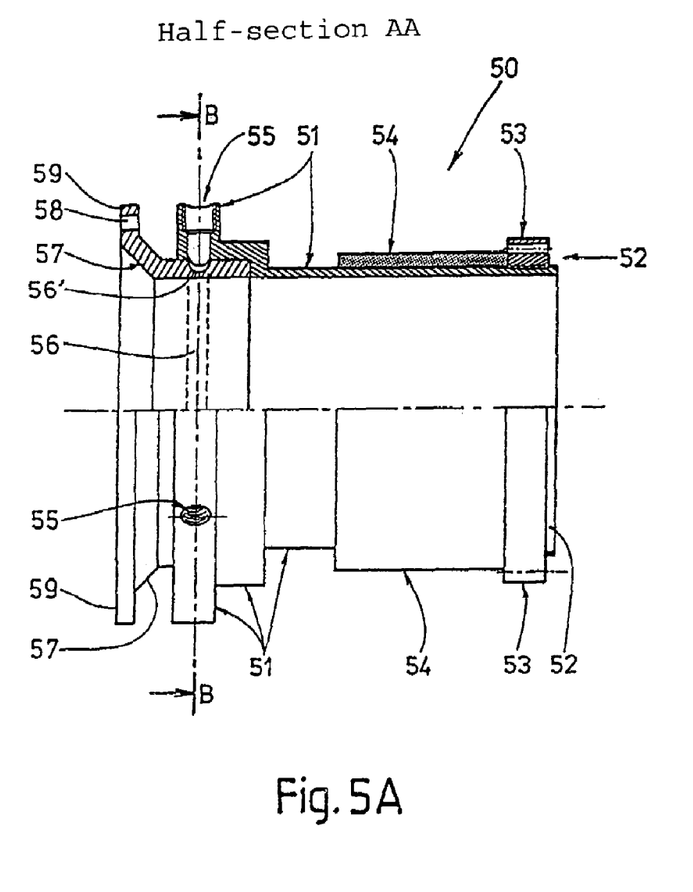
FIG. 5A shows a half-axial section and a semi-profile of an advantageous embodiment of a declutchable drive mechanism for the sample-holding cage of the device according to the invention.

In the example embodiment in FIGS. 2A and 5A, the crown wheel or the drive plate is attached by screws onto a nut 53 locked to the screw pitch of hub.

The nut 53 can also block a cylindrical spacer 54 in contact with the ball bearing ring 5 or the circular periphery of the ring plate 3.

Since the other end 55 of the hub is flared, the hub is then fixed in rotation with respect to the fixed support ring plate 3.

Finally, and advantageously, the cage 40 is connected to the hub through a declutchable mechanism.

The hub 50 is thus composed of two concentric bodies 57 and 51 with flared ends 59 and 55, that nest into each other.

As illustrated in FIG. 5A, the body 57 of the hub 50 has a flared funnel shape and terminates in a plane circular end 59, in which a screw thread 58 is formed to fix the cage 40 using the washer.

The other cylindrical end of the body 57 of the hub 50 is hollowed out to contain an annular groove 56 around its periphery.

Figure 5B:
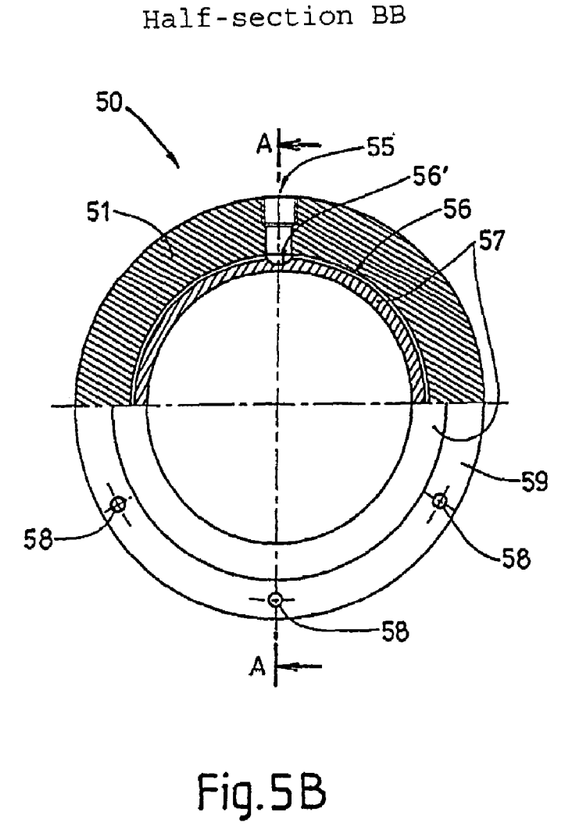
FIG. 5B shows a half-cross sectional and front view of the declutchable drive mechanism in FIG. 5A, and, FIG. 6 shows a principle diagram for the electrical power supply and temperature slaving circuit for the device according to the invention.
Figure 6:
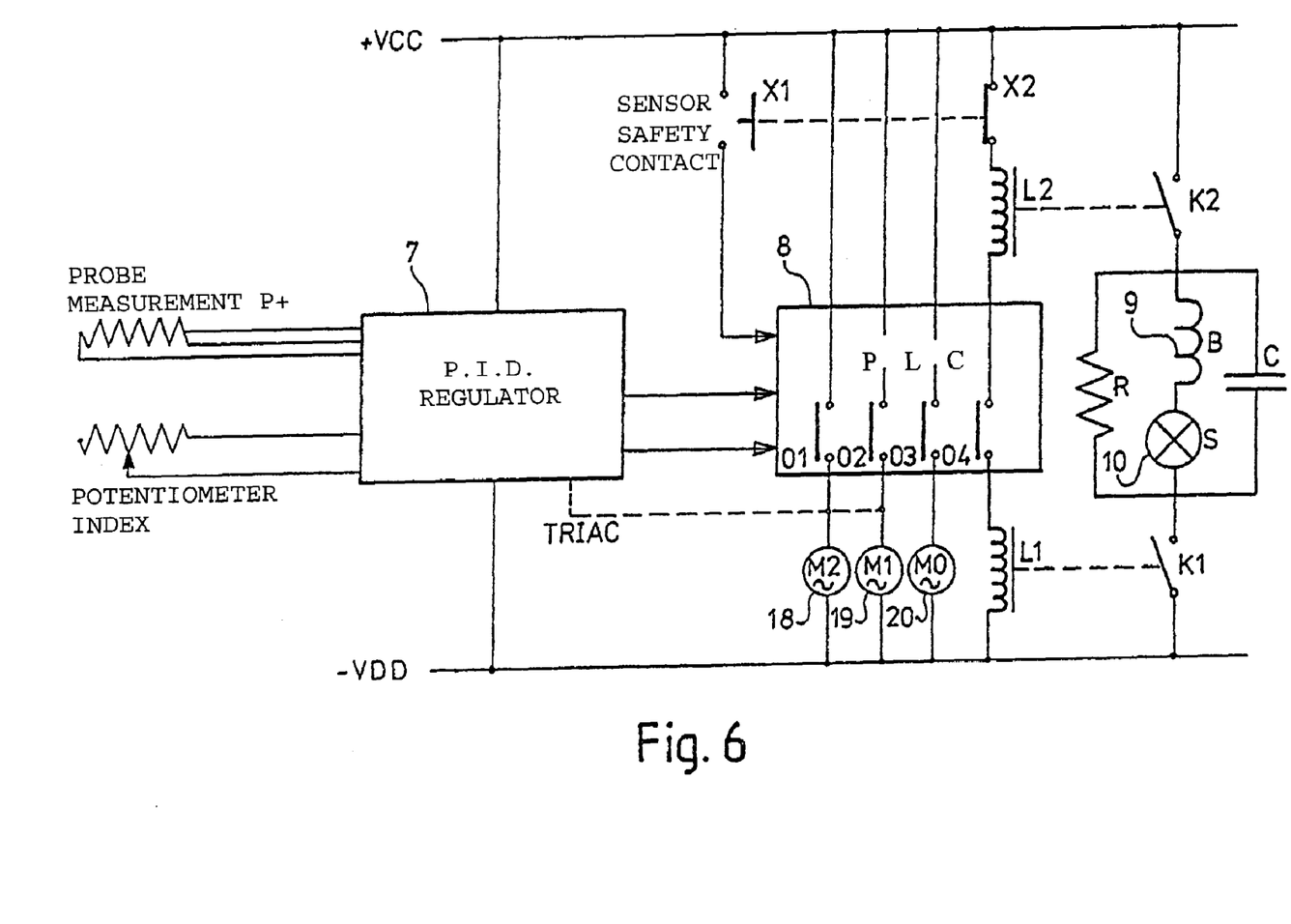

Furthermore, the annular groove 56 is hollowed out by several hemispherical cavities 56' at several points around its periphery to increase the depth of the groove 56. According to the example shown in FIG. 5, three cavities 56' will thus be provided equidistantly, at 120° from each other, around the periphery of the annular groove 56.

Similarly, the flared end of the main body of the hub 50 is perforated radially by tubular housings corresponding to the cavities 56' increasing the depth of the groove 56 in the end of body 57 also called end body.

Each housing will contain a ball and a spring held in place by a pressure adjustment screw.

Therefore when the end body 57 is inserted in the main body 51 of the hub 50, each ball will engage in the annular groove 56 and will then be blocked at the bottom of the corresponding hemispherical cavity 56'.

Since the balls are held in place at the bottom of the cavities 56' hollowed out in the groove 56, this mechanism provides a means of blocking the body end 57 in translation and in rotation with respect to the body 51 of the hub, in the same way that a lock insert is keyed in a lock cylinder.

However, if excessive torque is applied to the end body 57 with respect to the body 51 of the hub 50, the balls will be pushed out of their cavities 56' and the body 57 will be able to turn freely about the main body 51, with the balls remaining engaged in the annular groove 56.

This mechanism very advantageously enables declutching of the cage 40 in rotation with respect to the hub 50, when an excessive axial torque is applied between the cage and the hub.

Advantageously, this declutchable mechanism enables an operator to rotate the cage 40, even when the motor 20 is stopped.

Similarly, this mechanism prevents the motor 20 from being damaged when the cage 40 is accidentally blocked in rotation.

Furthermore, this mechanism very advantageously enables decoupling in translation between the cage 40 and the hub 50 when excessive axial tension is applied on the cage.

When an axial tension is applied forwards on the end body 57, the balls thus eventually escape from the bottom of the annular groove 56 and the end body 57 separates from the main body 51 of the hub 50.

Therefore, this mechanism provides a means of retracting or declutching the cage from the device, in translation.

Finally, each housing has one end clamped at a diameter less than the diameter of the balls, to prevent the balls from escaping from the housings when the end body 57 is separated.

Furthermore, according to one essential improvement, the device according to the invention includes a water tank in which the lower portion of the rotating cage is immersed.

A crescent-shaped basin 6 can thus be fixed to the bottom of the ring plate 3 of the device, the cage 40 being partially immersed in water 6' filling the basin 6.

This type of arrangement provides a means of testing the resistance of samples to weathering under the combined action of moisture, immersion in water and photonic radiation such as ultraviolet radiation, which advantageously includes most natural weathering agents, as will become clear in improvements to the invention that lead to the optimum embodiment of the invention that will be described below.

DETAILED DESCRIPTION OF THE OPTIMUM EMBODIMENT

Thus, according to the optimum embodiment a tank (in other words a basin or a reservoir) that will contain a liquid, particularly water or various aqueous compositions, is arranged on the inside of the chamber such that the sample-holding cage is partially immersed in the liquid contained in the tank.

The tank is rigidly fixed to the ring plate 3 of the partition in the lower part of the chamber.

The tank is preferably a crescent-shaped basin to match the cylindrical chamber and cage. Other shapes could be adopted depending on the shape of the chamber.

The width and the vertical depth of the tank are sufficiently large so that they surround a fairly large portion of the cage.

Typically, the useful height of the tank is of the order of one third of the radial dimension of the cage, but the useful height can reach higher values, up to the value of the radius of the cage.

This height is such that a lower portion of the cage corresponding to an angular sector of 120° C., or even greater values up to an angle of nearly 180° C., can be immersed.

The tank is provided with a filling system and an evacuation system that can conveniently be installed through the vertical partition of the ring plate of the chamber. For example, the system may include an inlet nozzle for water or another liquid, while the bottom of the tank is connected to a drain pipe through an outlet plug.

The liquid inlet pipe may be connected through a multi-way valve to several ducts so that additives can be mixed into the liquid as described below.

At the same time or alternatively, a sprinkler header pipe may be installed above the tank to sprinkle the samples and fill the tank.

Finally, a liquid level gauge is fitted in the tank, based on one of many gauge principles such as a float level, resistivity measurement, well known to those skilled in the art.

During operation, the level of the liquid in the tank shall be kept constant so that samples can be dipped during the determined time period.

Thus, the tank can be filled to a useful depth P such that a lower sector of the cage with an extent of about 120° C. corresponding to one third of the perimeter of the cage, can be immersed in the tank.

As the cage rotates, the samples then alternate through immersion phases in the liquid of the tank and emersion phases in the upper part of the chamber where they are exposed to the air stream. Samples are thus exposed to immersion for one third of the test duration.

The result is thus a series of alternating periods of dry exposure and periods during which the samples are immersed, which very naturally corresponds to real weather cycles.

Advantageously, the duration and proportion of sample immersion phases can be varied using an appropriate control system to vary the liquid level.

In practice, the duration of the immersed phase can be varied in proportions varying from one tenth or even a few hundredths of the duration of the cage rotation cycle, up to one third of this duration.

The duration of the immersed and emersed phases of the samples depends on the cage rotation speed.

In practice, the cage rotation speed is relatively small or even very small, since it is of the order of one tenth of revolution per hour to ten revolutions per hour, and in any case is less than one revolution per minute.

Advantageously, these speeds enable the required degradation phenomena to be set up, given that daily cycles and rain periods are of the same order of magnitude.

Thus standard ISO 4892.3 suggests that 8-hour dry exposure cycles should be alternated with 4-hour condensation exposure cycles.

The advantage of the device is that it can be used to vary degradation factors, namely exposure to the air stream in the chamber and immersion in the liquid in the tank, over wide ranges, which advantageously enables the results of accelerated artificial weathering to be compared with the results of natural weathering so that relevant test protocols can be validated. The purpose of this description is not to define these protocols, which must be defined by persons with experience in the subject through studies and standards.

The other essential advantage of the improved device according to the invention is that it is capable of reproducing, but particularly adding and combining different known degradation factors for which separate experiments are normally carried out.

Alternating phases may be adopted in which the samples are exposed to light and to air and are then immersed, followed by a phase in which the samples are kept dark while exposed to air and then immersed.

But it can be seen that photonic exposure continues during the immersion phases.

Therefore, the two known degradation factors, moisture and illumination, are combined simultaneously.

U.V. radiation emitted by the arc lamp passes through water practically without absorption.

Subsequently, when the samples are in the tank under a water depth, they are continuously exposed to photonic radiation from the central source, and particularly to ultraviolet radiation.

It is known that some degradation mechanisms require the simultaneous presence of several factors otherwise they will not be perpetuated.

According to known models, polymer degradation mechanisms comprise an initiation step in which the light energy of U.V. photons is involved.

But before the mechanism can continue indefinitely, the initiation reaction must be immediately followed by propagation reactions that involve oxygen. In particular, oxygen is supplied by water in the form of dissolved oxygen. These propagation reactions are completed by termination reactions in which cross-linking between polymer chains is possible.

The cross-linking reactions have the greatest effect on the colour, appearance and properties of the polymers. Therefore, these reactions are sought after during test campaigns.

In the absence of water and oxygen, the initiation step takes place with no effect and propagation reactions do not continue. The degradation mechanism then remains inactivated.

Thus with the improved device according to the invention, it is possible to essentially combine exposure to photonic radiation with immersion in water, and to accelerate these degradation mechanisms.

Therefore it is particularly advantageous to be able to combine exposure to photonic radiation with exposure to immersion.

Water thus acts as an oxygen activator. This is why normalized tests allow for exposure phases to humidity usually carried out by condensation or sprayed by sprinklers using devices known in standard practice.

Standards ISO-4892 specify that pure water should be used.

This arrangement corresponds to the capabilities of known devices since sprinklers require the use of water without any impurities, and condensation is also formed with pure water.

On the contrary, with the device according to the invention, it is possible to test liquid media that advantageously accelerate degradation phenomena.

Thus, in an unusual manner, according to the invention test protocols can be carried out in which the liquid may be water containing dissolved oxygen, or a liquid containing oxygenated water.

The invention can be used to test the exposure of samples to pure water, or to other liquids.

It is preferable to avoid the use of undiluted oxygenated water or excessively concentrated oxygenated water. Oxygenated water is an excessively powerful activator that could introduce degradation phenomena that do not occur in reality.

Thus, the immersion phase takes place in a water bath containing a proportion of oxygenated water.

Accessorily, since oxygenated water can decompose under the effect of UV rays, the insolation protection cover can be used to protect the liquid bath containing oxygenated water against UV radiation.

In practice, oxygenated water does not decompose.

Therefore, it is advantageous to include combined exposure to immersion in partially oxygenated water and photonic radiation in a single phase, so that the above-mentioned degradation phenomena can be observed.

Finally, the improved test process according to the invention advantageously allows for test protocols in which the liquid used is acidulated water.

Advantageously, this protocol is capable of reproducing climatic exposure to acid rain.

The process is also capable of performing test protocols in which the liquid is water containing suspended solids.

These arrangements mean that interaction of solid materials involved in degradation phenomena can be tested.

The use of a tank containing a liquid advantageously means that interaction with solid particles can be tested, which are degradation factors that are prohibited in sprinkling systems and condensation systems known in the state of the art, and by recommendations in standard ISO-4892.

Finally, the improved test process according to the invention makes it possible to use test protocols with phases in which the liquid in which the sample-holding cage is immersed is water containing pollutants.

Thus for information, the following pollutants could be added to the water:
   ozone,
   carbon dioxide,
   carbon oxides,
   sulphur trioxide and sulphur dioxide,
   chlorides,
   fluorine and phosphorus compounds,
   insecticides, pesticides and,
aerosols.

More generally, with the invention it is particularly useful if complete tests are carried out in which samples are exposed to different test protocols presented in this description.

The protocols may be applied in sequence to include all degradation phenomena.

Even better, with the invention, several of these test protocols can be combined simultaneously in order to observe real degradation mechanisms.

Therefore, this application is not restricted to the protocols described above, but also explicitly includes the various combinations of these protocols with each other.

Finally, test processes using the device for exposure to photonic radiation and climatic agents, improved according to the invention, thus provide a means of exhaustively carrying out tests on all identified degradation factors listed in standard ISO-4892, namely:
 the lamp filters,
 the irradiation level,
 the temperature,
 exposure to water,
 temperature,
 exposure to water,
 water exposure cycles and temperatures,
 timing of illumination and darkness cycles, and
 timing of dry and wet cycles.

Other protocols, processes, embodiments, variants and improvements could be made by those skilled in the art without going outside the framework of this invention, the subject of the protection being defined in the following claims.

The invention claimed is:

1. Device for exposure of samples to photonic radiation for accelerated artificial weathering tests, comprising:
 a chamber,
 a sample-holding cage rotating around an axis (H—H) that will be approximately horizontal in operation,
 means of fixing the position of at least one arc lamp, and particularly a mercury vapour lamp or a mercury or compound vapour lamp near the central part of the cage, and of supplying said lamp with electricity,
 an air circulation system comprising an air passage orifice arranged along the axial prolongation (H—H) of the central part of the cage and several fixed air passage openings arranged in the radial prolongation of the periphery of the cage,
 the improvement being that a ventilation means blows air into the chamber through the orifice that forms an air intake orifice arranged approximately parallel to the horizontal axis (H—H), the lamp being placed along the immediate axial prolongation (H—H) of the air intake orifice, so as to generate an air stream arriving directly on the lamp and approximately parallel to the axis along the central part of the cage, the air stream diverging around the lamp and being evacuated approximately perpendicular to the axis through the fixed air passage openings that form air openings around the periphery of the cage, such that the temperature of the air stream increases as the air stream comes into contact with the lamp, before going around the samples, increasing their temperature.

2. Device according to claim 1, in which the cage is installed free to rotate on a hub hollowed out along the axial direction (H—H), the air stream being blown through the axial hole through the hub.

3. Device according to claim 2, in which ventilation means are arranged in the hollowed out hole in the hub, so as to blow air towards the chamber.

4. Device according to claim 2, in which the cage is connected to the hub through a declutchable drive mechanism allowing free rotation of the cage.

5. Device according to claim 4, in which the mechanism comprises rotation declutching means under the effect of a limited axial torque between the cage and the hub.

6. Device according to claim 1, in which the air stream: diverging around the lamp comprises essentially a component approximately parallel to the axis (H—H), in the central part of the cage close to the lamp, while the said air stream comprises essentially components approximately perpendicular to the axis, at the periphery of the cage near the samples.

7. Device according to claim 1, further comprising cage rotation drive means and in which all lamp positioning means and power supply means, ventilation and air circulation means and cage rotation drive means are arranged in line along the horizontal axis (H—H) of the device.

8. Device according to claim 1, in which the air circulation system comprises a series of several fixed air passage openings arranged regularly around the periphery of the cage with a symmetry of revolution about the axis (H—H), each fixed air passage opening being oriented in a direction between the radial direction and the tangential direction around the periphery of the cage.

9. Device according to claim 1, in which the cylindrical chamber comprises air passage openings arranged approximately at the periphery of the cage, each air passage opening being oriented in a non-radial direction and with a depth, aperture and angle of inclination relative to the radial direction, such that the radiation from each lamp positioned in the central part of the cage does not pass through the air passage opening and does not escape directly outside the chamber.

10. Device according to claim 1, comprising a tank arranged in the lower part of the device and intended to contain a liquid volume so that a lower portion of the rotating sample-holding cage can be immersed, such that the samples cyclically alternate between immersion phases in the liquid and emersion phases in the air stream.

11. Device according to claim 1, in which the air circulation system comprises means of heating the air stream.

12. Device according to claim 1, in which a water sprinkling header pipe projects inside the cage so as to sprinkle the exposed inner face of the samples.

13. Method for carrying out accelerated artificial weathering tests on samples, in which the samples are exposed to photonic radiation and climatic agents, characterised in that the method includes steps of:
 arranging the samples on a sample-holding cage rotating about an approximately horizontal axis (H—H),
 positioning at least one photonic radiation lamp in a fixed position in the central part of the cage along the horizontal rotation axis (H—H),
 supplying electrical power to said lamp,
 generating a simple direct air stream arriving directly on the lamp propagating approximately parallel to the axis, the air stream diverging around the lamp and being evacuated approximately perpendicular to the horizontal axis (H—H) at the periphery of the sample-holding cage, such that the air stream temperature increases on contact with the lamp, before surrounding the samples, and providing a liquid bath at a lower portion of the rotating sample-holding cage, so as to cyclically alternate phases in which the samples are immersed in the liquid and phases in which the samples are exposed to the air stream.

14. Test method according to claim 13, in which the lower portion of the cage is immersed in a tank that can contain a liquid volume.

15. Test method according to claim 13, in which the air stream is a turbulent stream about the approximately horizontal axis of rotation (H—H), the air stream in the central part of the cage being moved in translation with a component approximately parallel to the axial direction (H—H), the air stream being moved in rotation at the periphery of the cage, each component being in a direction between the radial direction and the tangential direction.

16. Test method according to claim 13, comprising a test protocol consisting of:

measuring and regulating the temperature of a reference element by a temperature regulation acting on the electrical power supply to the lamp and/or the air stream generation means.

17. Test method according to claim 13, comprising a test protocol with immersion phases in which the liquid in which the sample-holding cage is immersed is water containing dissolved oxygen.

18. Test method according to claim 13, wherein the liquid is water containing one or more pollutants chosen from among the group of pollutants comprising ozone, carbon dioxide, nitrogen oxides, sulphur trioxide and sulphur dioxide, chlorides, fluorine compounds, phosphorus compounds, insecticides, pesticides and aerosols.

* * * * *